United States Patent [19]

Matsumoto et al.

[11] Patent Number: 5,637,741
[45] Date of Patent: Jun. 10, 1997

[54] PROCESS FOR PRODUCING 2-METHYL-1,4-NAPHTHOQUINONE

[75] Inventors: Yoichi Matsumoto, Kurashiki; Kozo Nakao, Yokohama, both of Japan

[73] Assignee: Kuraray Co., Ltd., Kurashiki, Japan

[21] Appl. No.: 529,455

[22] Filed: Sep. 18, 1995

[30] Foreign Application Priority Data

Sep. 27, 1994 [JP] Japan ................ 6-257545
Nov. 16, 1994 [JP] Japan ................ 6-306904

[51] Int. Cl.⁶ .................................................. C07C 50/12
[52] U.S. Cl. ................................................. 552/299
[58] Field of Search .................................... 552/299

[56] References Cited

U.S. PATENT DOCUMENTS

| | | | |
|---|---|---|---|
| 3,751,437 | 8/1973 | Huba | 552/299 |
| 3,953,482 | 4/1976 | Sugano et al. | 552/299 |
| 4,906,411 | 3/1990 | Shinnaka et al. | 552/299 |
| 5,075,463 | 12/1991 | Kuo et al. | 552/299 |

FOREIGN PATENT DOCUMENTS

| | | | |
|---|---|---|---|
| 60-252445 | 12/1985 | Japan | 552/299 |
| 61-227548 | 10/1986 | Japan | 552/299 |

OTHER PUBLICATIONS

Patent Abstracts of Japan, vol. 11, No. 69 (C–407), Mar. 3, 1987, JP–61–227548, Oct. 9, 1986.

Database WPI, Derwent Publications Ltd., AN–78–43081A, JP–53–050147, May 8, 1978.

*Primary Examiner*—James H. Reamer
*Attorney, Agent, or Firm*—Oblon, Spivak, McClelland, Maier & Neustadt, P.C.

[57] ABSTRACT

The present invention provides a process for producing 2-methyl-1,4-naphthoquinone characterized by reaction between 2-methylnaphthalene and hydrogen peroxide and/or an organic peracid in a solvent comprising a carboxylic acid in the presence of a palladium compound and sulfuric acid.

9 Claims, No Drawings

PROCESS FOR PRODUCING 2-METHYL-1,4-NAPHTHOQUINONE

BACKGROUND OF THE INVENTION

1. Field of the Invention

The present invention relates to a process for producing 2-methyl-1,4-naphthoquinone by oxidation of 2-methylnaphthalene in liquid phase.

2-Methyl-1,4-naphthoquinone, sometimes called menadione or vitamin K3, has anti-hemorrhagic activity. Many derivatives of 2-methyl-1,4-naphthoquinone including vitamins K1, K2, K4, sodium bisulfite adduct of vitamin K3 and dimethylpyrimidinol bisulfite adduct of vitamin K3 have been employed as medicines for human and additives for animal feed and are thus useful.

2. Related Art of the Invention

Typical of known industrial processes of producing 2-methyl-1,4-naphthoquinone is a process wherein 2-methylnaphthalene is oxidized by use of chromic anhydride or bichromates such as sodium bichromate. However, the ecological problem caused by chromium compounds has made it difficult to produce 2-methyl-1,4-naphthoquinone by the process in these days.

On the other hand, many attempts have been made for oxidation processes which don't use any chromium compound. One of such attempts is a process wherein 2-methylnaphthalene is oxidized, in vapor phase, with oxygen by use of a vanadium-based catalyst (see Japanese Patent Laid-open No. Hei 6-9485). In order to attain high selectivity, the conversion has to be suppressed to a very low level in this process.

For an oxidation process in liquid phase, there is a process using cerium compounds (see U.S. Pat. No. 4,840,749). According to this process, the intended compound can be obtained at a relatively high yield. However, because a stoichiometric amount of a cerium compound is used, it is required to regenerate the cerium compound, for example, by electrolysis.

Other known processes include processes wherein 2-methylnaphthalene in liquid phase is oxidized by use of hydrogen peroxide or organic peracids. The reaction procedures in the processes include a procedure wherein oxidation is conducted in a solvent, such as acetic acid, without use of any catalyst (see Japanese Patent Publication No. Sho 59-53252) and a procedure wherein acids are used as a catalyst (see Japanese Patent Laid-open No. Sho 53-50147). In either case, the yield is as low as less than 40%. An attempt has been made to use, as a catalyst, ion-exchange resins deposited with palladium (see Japanese Patent Laid-open No. Sho 61-227548). In this process, a high yield exceeding 50% is attained. However, a great amount of ion-exchange resins is used relative to the reactant. From the standpoint of the cost for the ion-exchange resin and the prevention of contamination by impurities from the ion-exchange resin, it is necessary to impart very high durability to the ion-exchange resin. Test results are reported in Chem. Pharm. Bull., 34(2), 445–449 (1986), where oxidation of 2-methylnaphthalene with hydrogen peroxide and the recycled palladium ion-exchange resin catalyst in an acetic acid is conducted repeatedly. According to the report, the yield is 60.2% for the first cycle and is 50.5% for the fourth cycle, thus lowering by about 16%. The follow-up test made by us revealed that the catalytic activity was lost after 5 to 6 maximum repetitions in use. This means that the cost for the catalyst becomes very high, making it difficult to industrially adopt this process from an economical point of view. Where ion-exchange resins are used in batchwise reactors, the ion-exchange resin is stirred along with a reaction solution and, thus, should have appropriate physical strength. On the other hand, when ion-exchange resins are employed in a continuous reactor, removal of the heat is very difficult, since the reaction is highly exothermic. To attain a satisfactory conversion of 2-methylnaphthalene according to this process, hydrogen peroxide has to be used in amounts of not less than 6 times by mole relative to the 2-methylnaphthalene, that is twice the theoretical amount. This will not only cause a high ratio of the cost of hydrogen peroxide to the total cost of starting chemicals, but also bring about generation of oxygen gas caused by the decomposition of excessive hydrogen peroxide and/or accumulation of the peroxide in the reaction system, with the great possibility of ignition and explosion during the course of running operations.

SUMMARY OF THE INVENTION

The object of the present invention is to provide a process for producing 2-methyl-1,4-naphthoquinone by oxidation of 2-methylnaphthalene with an oxidizing agent such as hydrogen peroxide wherein not only the yield from 2-methylnaphthalene is improved, but also the oxidizing agent is more efficiently utilized, the reaction system is made so homogeneous as to permit easier removal of heat, and the cost of a catalyst is reduced whereby 2-methyl-1,4-naphthoquinone is produced more economically and more industrially beneficially than in prior art processes.

The object of the invention can be achieved by the present invention described below. The present invention contemplates to provide a process for producing 2-methyl-1,4-naphthoquinone which is characterized by subjecting hydrogen peroxide and/or an organic peracid to reaction with 2-methylnaphthalene in a solvent containing a carboxylic acid in the presence of a palladium compound and 5 to 100 g of sulfuric acid per liter of the carboxylic acid.

DETAILED DESCRIPTION OF THE INVENTION

The present invention is described in detail.

2-Methylnaphthalene used as a starting material in the present invention is industrially produced, for example, by methods such as of separation from tar fractions and can be readily commercially available.

The carboxylic acids used as the solvent in the present invention may be ones which are miscible with the starting material and sulfuric acid and which are liquid under reaction conditions. Particularly, acetic acids, propionic acid, butyric acid, caprylic acid, caproic acid, capric acid and the like are exemplified. Ordinarily, inexpensive acetic acid is preferred because of its good compatibility with the starting material, product, by-products, sulfuric acid, hydrogen peroxide, formed water and the like.

The carboxylic acids may be used alone or in combination with solvents inert to the reaction.

The palladium compounds used in the present invention should favorably be capable of forming a homogeneous system on addition to the reaction system. In particular, mention is made of carboxylates such as palladium acetate, palladium caprylate and the like, halides such as palladium chloride, palladium bromide and the like, acid salts such as palladium sulfate, palladium nitrate and the like, and complexes such as palladium acetylacetonate, dichlorobis (triphenylphosphine) palladium, tris(dibenzylideneacetone) dipalladium (0) chloroform adduct and the like. Of these, palladium acetate and palladium sulfate are preferred.

The palladium compounds may be used alone or in combination.

If the amount of a palladium compound is too small, satisfactory results cannot be obtained with respect to the yield and the efficiency of hydrogen peroxide. The use of a large excess of palladium compound is not favorable from the economical point of view. Accordingly, the amount of a palladium compound is generally in the range of 25 to 500 mg/liter, preferably 45 to 200 mg/liter when calculated as the amount of palladium per total volume of a solvent.

Sulfuric acid used for the reaction may be either concentrated sulfuric acid or an aqueous sulfuric acid. Alternatively, sulfuric acid may be used in the form of a solution in a carboxylic acid.

Sulfuric acid is used in the range of 5 to 100 g, preferably 15 to 50 g, per liter of a carboxylic acid. If the amount of sulfuric acid is too small, 2-methyl-1,4-naphthoquinone cannot be obtained in a satisfactorily high yield. On the contrary, too great an amount is unfavorable from the standpoint of costs and corrosion of an apparatus.

Hydrogen peroxide used as an oxidizing agent is usually employed in the form of an aqueous solution having a concentration of 30 to 60 wt %. Of course, 100% hydrogen peroxide may be used. Besides, organic peracids such as peracetic acid, m-chloroperbenzoic acid and the like may also be used. The organic peracids may be used in a pure form or in the form of a solution diluted with an appropriate solvent. Alternatively, hydrogen peroxide has been preliminarily reacted with carboxylic acids to provide organic peracids. This peracid may be used for oxidation directly. If the amount of hydrogen peroxide and/or organic peracid is too small, a satisfactory conversion of a starting material cannot be attained. Greater amounts are disadvantageous not only in economy, but also in that excess hydrogen peroxide and/or organic peracid acts to further oxidize the product, resulting in a lowering of yield. A preferable amount of hydrogen peroxide and/or organic peracid is in the range of 0.5 to 10 mols, more preferably from 1 to 4 mols, per mole of 2-methylnaphthalene. The manner of addition of hydrogen peroxide and/or organic peracid is such that a given amount of the peroxide and/or organic peracid is added to a reaction system at one time. Alternatively, hydrogen peroxide and/or organic peracid may be added gradually at a constant rate. Still alternatively, hydrogen peroxide and/or organic peracid may be added after mixing with a carboxylic acid solvent or a mixture of a carboxylic acid and sulfuric acid.

When 2-methylnaphthalene which is a starting material is present in a solution at too high a concentration, the yield of 2-methyl-1,4-naphthoquinone decreases. Too low a concentration results in a poor volumetric efficiency, thus being inconvenient for practical applications. In general, the concentration of 2-methylnaphthalene is in the range of 0.1 to 200 g/liter, preferably 1 to 100 g/liter, when expressed in terms of an amount relative to a volume of final solution.

The reaction temperature preferably ranges from 25° C. to 100° C., more preferably from 40° to 90° C. If the reaction temperature is lower than 25° C., the yield of 2-methyl-1,4-naphthoquinone decreases. On the contrary, when the temperature exceeds 100° C., hydrogen peroxide and/or organic peracid start to decompose, resulting in a poor efficiency of reaction. Although the reaction time is generally in the range of 5 minutes to about 8 hours, the time can be arbitrarily controlled depending on the rate of addition of hydrogen peroxide and/or organic peracid and the reaction conditions.

It is preferred from the economical standpoint that the palladium compound used as catalys in the reaction is subjected to after-treatment for the purpose of recovery and re-use thereof. The after-treating methods include a method wherein a reducing agent is added so as to precipitate metallic palladium and a method wherein after dissolution in an appropriate solvent, palladium is adsorbed and collected. In the present invention, it is preferable for simplicity to collect and re-use palladium compound according to the following steps (a) to (d).

(a) A hydrogen sulfide gas, or a solution of hydrogen sulfide and/or a salt thereof is added to a reaction solution to convert a palladium compound used as a catalyst into an insoluble sulfur compound of palladium.

(b) The insoluble sulfur compound of palladium is separated from the solution.

(c) The thus separated sulfur compound of palladium is oxidized with hydrogen peroxide and/or an organic peracid in a carboxylic acid solvent and dissolved therein.

(d) The obtained carboxylic acid solution of the palladium compound is recycled for the oxidation reaction of 2-methylnaphthalene with hydrogen peroxide and/or an organic peracid.

In the step (a), hydrogen sulfide may be directly introduced into the reaction solution, or hydrogen sulfide and/or a salt thereof may be added after dissolution in carboxylic acids or water. Typical salts of hydrogen sulfide include alkali metal salts such as sodium sulfide, sodium hydrogensulfide, potassium hydrogensulfide and the like. The salts should preferably be soluble in water or carboxylic acids.

In principle, hydrogen sulfide and/or salts thereof are used in an equimolar amount relative to the palladium compound serving as a catalyst. However, peroxides such as hydrogen peroxide and organic peracids present in the reaction solution may oxidize hydrogen sulfide and/or salts thereof with the possibility of preventing insolubilization of palladium compounds. Accordingly, hydrogen sulfide and salts thereof are added in greater amount than an equimolar relative to the palladium compound, e.g. they are added in excess by an amount corresponding to approximately ¼ mols of active oxygen from the peroxide in the reaction solution to reduce the peroxide therewith. By this, the palladium compound is permitted to be insolubilized and separated satisfactorily. It will be noted that the reduction of the peroxide in the reaction solution may be effected by use of reducing agents other than hydrogen sulfide or salts thereof, e.g., sodium thiosulfate.

The temperature and other conditions where a solution of hydrogen sulfide and/or salts thereof is added to the reaction solution are not critical. Usually, the palladium compound in the reaction solution is insolubilized within several minutes after addition of hydrogen sulfide and/or salts thereof.

It is preferred that prior to the addition of hydrogen sulfide and/or salts thereof, the sulfuric acid in the reaction solution is neutralized.

The insolubilized sulfur compound of palladium is separated from the reaction solution in the step (b) according to usual procedures such as filtration, centrifugal separation, decantation and the like. If the insolubilized sulfur compound of palladium is in the form of fine particles, appropriate filter aids may be used.

The sulfur compound of palladium separated in the step (b) is suspended, in the step (c), in a carboxylic acid solvent of the same type as used for the oxidation reaction of 2-methylnaphthalene. Hydrogen peroxide and/or an organic peracid is added to the resultant suspension, followed by heating, to obtain a homogeneous solution. The hydrogen peroxide and/or organic peracid may be added to the suspension at one time or may be added gradually. If the amount of hydrogen peroxide and/or an organic peracid is too small, the sulfur compound of palladium is not completely dissolved.

The carboxylic acid solution of the palladium compound obtained in the step (c) is recycled as it is or, if necessary, after further addition of a fresh starting material, a solvent and sulfuric acid, for the oxidation reaction of 2-methylnaphthalene with hydrogen peroxide and/or an organic peracid in the step (d). Where the concentration of the palladium compound in the carboxylic acid solution recycled in the step (d) is lower than as desired, the solution should be preliminarily concentrated to a given level.

Thus, the homogeneous solution comprising the palladium compound obtained in the step (c) is readily re-used at a high ratio of recovery. Hence, the collection and re-use of the palladium compound used as catalyst can be performed simply.

It will be noted that the collection of the palladium compound involves a loss of the compound in a small amount. Such a loss can be made up by addition of a fresh palladium compound, if necessary.

2-Methyl-1,4-naphthoquinone formed by the oxidation reaction of 2-methylnaphthalene with hydrogen peroxide and/or an organic peracid is isolated from the reaction mixture by any of ordinarily known methods. For instance, the reaction solution is concentrated, to which water is added to permit 2-methyl-1,4-naphthoquinone to be precipitated as solids.

Where the palladium compound is collected in a manner as described hereinbefore, the insolubilized sulfur compound of palladium is first separated from the reaction solution, followed by isolation of the 2-methyl-1,4-naphthoquinone from the reaction mixture. This is preferred from the standpoint of the recovery of the palladium compound.

According to the present invention, 2-methyl-1,4-naphthoquinone is obtained through a one-step reaction at high selectivity without a sacrifice of conversion of the starting material.

Moreover, a high conversion is attained using hydrogen peroxide and/or organic peracid in an amount corresponding to approximately the theoretical. The efficiency of hydrogen peroxide can be drastically enhanced in comparison with known processes which make use of palladium and ion-exchange resins in the oxidation of 2-methylnaphthalene with hydrogen peroxide. Thus, 2-methyl-1,4-naphthoquinone can be produced conveniently from the standpoint of economy and safety.

Furthermore, according to the present invention, the reaction is carried out in a homogeneous system under mild conditions, so that removal of heat from the reaction system is easy. Since neither expensive ion-exchange resin which is liable to degrade in the reaction system nor chromium compound, which presents an environmental problem is used, 2-methyl-1,4-naphthoquinone can be produced in an industrially advantageous manner.

Other features of the present invention will become apparent in the course of the following descriptions of exemplary embodiments which are given for illustration of the present invention and are not intended to be limiting thereof.

EXAMPLES

In the following examples, 2-methylnaphthalene and 2-methyl-1,4-naphthoquinone may be sometimes abbreviated as MN and VK3, respectively. The conversion, selectivity and yield were, respectively, determined according to the following equations.

$$\text{Conversion (\%)} = \frac{\text{mols of converted } MN}{\text{mols of fed } MN} \times 100$$

$$\text{Selectivity (\%)} = \frac{\text{mols of formed } VK3}{\text{mols of converted } MN} \times 100$$

$$\text{Yield (\%)} = \frac{\text{mols of formed } VK3}{\text{mols of fed } MN} \times 100$$

Example 1

0.7 g (4.92 mmols) of 2-methylnaphthalene (MN) and 800 mg of sulfuric acid (20 g per liter of total acetic acid) were dissolved in 13 ml of acetic acid, to which 4.0 ml of an acetic acid solution of 0.2% of palladium acetate was added, followed by heating to 70° C. under agitation and a mixture of 0.7 ml (15.32 mmols) of a 60% aqueous hydrogen peroxide and 3.0 ml of acetic acid was added dropwise in 15 minutes. After completion of the addition, the reaction solution was agitated at 70° C. for 15 minutes, followed by cooling of the reaction solution and quantitative determination of the starting material and the product according to an HPLC internal standard method. As a result, it was found that the conversion of 2-methylnaphthalene was 96.2%, the selectivity to 2-methyl-1,4-naphthoquinone (VK3) was 67.3%, and the yield was 64.7%.

Examples 2 to 6

The general procedure of Example 1 was repeated except that sulfuric acid was used in amounts indicated in Table 1 and the reaction time after completion of the addition was 1 hour. The results of the reaction are shown in Table 1.

TABLE 1

| Example | Amount of Sulfuric Acid (mg) | Conversion of MN % | Selectivity to VK3 (%) | Yield of VK3 % | Concentration of Sulfuric Acid (g/l) |
| --- | --- | --- | --- | --- | --- |
| 2 | 100 | 94.9 | 55.9 | 53.0 | 5 |
| 3 | 200 | 96.5 | 58.4 | 56.4 | 10 |
| 4 | 400 | 95.0 | 62.7 | 59.5 | 20 |
| 5 | 800 | 94.5 | 63.7 | 60.2 | 40 |
| 6 | 1600 | 94.4 | 63.6 | 60.1 | 80 |

Examples 7 and 8

MN, the amount of which was indicated in Table 2, and 400 mg of sulfuric acid were dissolved in 16 ml of acetic acid, to which 1.0 ml of an acetic acid solution of 0.2% of palladium acetate was added, followed by heating to 70° C. under agitation. Thereafter, mixtures of a 60% aqueous hydrogen peroxide ($H_2O_2$) in amounts indicated in Table 2 and 3.0 ml of acetic acid were, respectively, added dropwise in 15 minutes. After completion of the addition, the reaction solution was agitated at 70° C. for 1 hour and cooled down, followed by quantitative determination of the starting material and the product according to an HPLC internal standard method as in Example 1. The results of the reaction are shown in Table 2.

TABLE 2

| Example | Amount of MN (g) | Amount of H₂O₂ (ml) | Conversion of MN % | Selectivity to VK3 (%) | Yield of VK3 (%) |
|---|---|---|---|---|---|
| 7 | 0.3 | 0.3 | 93.4 | 68.4 | 63.9 |
| 8 | 0.7 | 0.7 | 90.3 | 63.1 | 57.0 |

Examples 9 to 11

0.7 g of MN and 400 mg of sulfuric acid were dissolved in 16 ml of acetic acid, to which 1.0 ml of an acetic acid solution of 0.2% of palladium acetate was added, followed by heating to predetermined temperatures indicated in Table 3 under agitation and dropwise addition of a mixture of 0.7 ml of a 60% aqueous hydrogen peroxide and 3.0 ml of acetic acid in 15 minutes. After completion of the addition, the reaction solution was agitated at such a temperature as indicated above for 1 hour (for 2.5 hours in Example 11). Thereafter, the reaction solution was cooled down and subjected to quantitative determination of the starting material and the product according to an HPLC internal standard method as in Example 1. The results of the reaction were shown in Table 3.

TABLE 3

| Example | Reaction Temperature (°C.) | Conversion of MN (%) | Selectivity to VK3 (%) | Yield of VK3 (%) |
|---|---|---|---|---|
| 9 | 80 | 88.2 | 59.9 | 52.9 |
| 10 | 70 | 90.3 | 63.1 | 57.0 |
| 11 | 50 | 90.7 | 57.3 | 51.9 |

Examples 12 to 15

0.7 g of MN and 400 mg of sulfuric acid were dissolved in 13 ml of acetic acid, to which predetermined amounts of an acetic acid solution of 0.2% of palladium acetate were, respectively, added, followed by further addition of acetic acid to make 17 ml, in total, of acetic acid in the solution. The reaction solution was heated to 70° C. under agitation, to which a mixture of 0.7 ml of a 60% aqueous hydrogen peroxide and 3.0 ml of acetic acid was added dropwise in 15 minutes. After completion of the addition, the solution was agitated at such a temperature as set out above for 1 hour, followed by cooling of the solution and quantitative determination of the starting material and the product according to an HPLC internal standard method as in Example 1. The amount of the added palladium acetate and the results of the reaction are shown in Table 4.

TABLE 4

| Example | Amount of Pd(OAc)₂ (mg) | Conversion of MN (%) | Selectivity to VK3 (%) | Yield of VK3 (%) |
|---|---|---|---|---|
| 12 | 8 | 95.0 | 62.7 | 59.5 |
| 13 | 4 | 92.3 | 65.0 | 60.0 |
| 14 | 2 | 90.3 | 63.1 | 57.0 |
| 15 | 1 | 89.0 | 56.0 | 49.8 |

Example 16

The general procedure of Example 14 was repeated except that 15 μl (8.9 μmols) of a 12% aqueous palladium sulfate was used in place of the acetic acid solution of palladium acetate. The results of the reaction revealed that the conversion of MN was 89.2% and the selectivity to VK3 was 60.3%.

Example 17

The general procedure of Example 14 was repeated except that 9.5 mg of tris(dibenzylideneacetone)dipalladium (0) chloroform adduct was used in place of the palladium acetate. The results of the reaction revealed that the conversion of MN was 92.5% and the selectivity to VK3 was 64.1%.

Example 18

The general procedure of Example 14 was repeated except that 6.2 mg of dichlorobis(triphenylphosphine) palladium was used in place of the palladium acetate. The results of the reaction revealed that the conversion of MN was 92.5% and the selectivity to VK3 was 62.5%.

Example 19

1.4 ml of a 60% aqueous hydrogen peroxide, 19.6 ml of acetic acid and 400 mg of sulfuric acid were reacted at 70° C. for 30 minutes while agitating. After completion of the reaction, the peracetic acid and hydrogen peroxide present in the solution were quantitatively determined through titration and found to be 1.24 mols/liter and 0.08 mols/liter, respectively. 10 ml of the obtained peracetic acid solution was used for the following reaction.

0.7 g of MN and 400 mg of sulfuric acid were dissolved in 20 ml of acetic acid, to which 1.0 ml of an acetic acid solution of 0.2% of palladium acetate was added, followed by heating to 70° C. under agitation and dropwise addition of 10 ml of the above peracetic acid solution in 15 minutes. After completion of the addition, the reaction solution was agitated at the same temperature as set out above for 1 hour. The reaction solution was cooled down and subjected to quantitative determination of the starting material and a product according to an HPLC internal standard method as in Example 1. The results of the reaction revealed that the conversion of MN was 79.6% and the selectivity to VK3 was 60.8%.

Example 20

The general procedure of Example 4 was repeated using propionic acid in place of all the acetic acid with the same amount. The results of the reaction revealed that the conversion of MN was 88.0% and the selectivity to VK3 was 60.3%.

Comparative Example 1

For comparison, the reaction was effected using sulfuric acid alone as a catalyst. More particularly, the general procedure of Example 14 was repeated except that palladium acetate was not added and the reaction time was 3 hours. As a result of analysis after the reaction, it was found that the conversion of MN was 80.0%, the selectivity to VK3 was 45.6% and the yield was 36.5%.

Comparative Example 2

For comparison, the reaction was effected using palladium acetate alone as a catalyst without addition of sulfuric acid. More particularly, the general procedure of Example 1 was repeated except that sulfuric acid was not added and the reaction time was 4 hours. As a result of analysis after the reaction, it was found that the conversion of MN was 57.7%, the selectivity to VK3 was 39.6% and the yield was 22.8%.

Comparative Example 3

Preparation of catalyst: 1 g of a sulfonic acid type ion-exchange resin (DOWEX 50W-X8 with a size of 200 to 400 meshes) was immersed in 10 ml of acetic acid, followed by removal the supernatant acetic acid through decantation. Thereafter, 10 ml of acetic acid was added to the resin, followed by addition of 2 mg of palladium acetate under agitation and further agitation for 5 hours as it is. After allowing to stand overnight, excessive acetic acid was removed.

Reaction: 10 ml of acetic acid and 0.35 g of MN were added to the above catalyst and heated to 50° C. while agitating, followed by addition of 0.35 ml of a 60% aqueous hydrogen peroxide to start the reaction. 4 hours after the reaction, 0.35 ml of a 60% aqueous hydrogen peroxide was further added, followed by continuing the reaction for further 4 hours. After cooling, the reaction solution was analyzed according to an HPLC internal standard method as in Example 1 to determine the results of the reaction, revealing that the conversion of MN was 75.4%, the selectivity to VK3 was 49.0%, and the yield was 36.9%.

Comparative Example 4

Using such a catalyst as produced in Comparative Example 3, the general procedure of Comparative Example 3 was repeated except that the amount of hydrogen peroxide was 0.35 ml which was initially used without further addition of hydrogen peroxide after 4 hours. As a result, it was found that the conversion of MN was 42.0%, the selectivity to VK3 was 44.2%, and the yield was 18.5%. Thus, satisfactory results could not be obtained. This means that about 80% of hydrogen peroxide used was consumed for side reactions such as decomposition of oxygen and oxidation of the product.

Comparative Examples 5 and 6

The general procedure of Example 4 was repeated except that other types of acids were used in place of sulfuric acid. The types and amounts of acids and the results of the reaction are shown below.

Comparative Example 5: phosphoric acid 800 mg (reaction time: 2 hours)

MN conversion: 64.2%, selectivity to VK3: 42.8%

Comparative Example 6: trifluoromethanesulfonic acid 800 mg

MN conversion: 86.4%, selectivity to VK3: 38.9%

Comparative Example 7

The general procedure of Example 2 was repeated except that sulfuric acid was used in an amount of 20 mg. The results of the reaction revealed that the conversion of MN was 80.9%, the selectivity to VK3 was 48.1%, and the yield was 38.9%. Thus, the MN conversion was not satisfactory and the selectivity to VK3 did not exceed 50%.

Example 21

(1) Oxidation reaction of 2-methylnaphthalene

A mixture of 8.75 g (61.5 mmol) of 2-methylnaphthalene (MN), 200 ml of acetic acid and 5.0 g (20 g/liter of total acetic acid) of sulfuric acid was heated to 70° C., to which 5.0 ml of an acetic acid solution of 0.5% of palladium acetate was added under agitation. Immediately, a mixture of 8.75 ml (191.5 mmol) of a 60% aqueous hydrogen peroxide and 45 ml of acetic acid was added dropwise in 15 minutes. After completion of the addition, the reaction solution was agitated at 70° C. for 15 minutes. After cooling, the reaction solution was analyzed according to an HPLC internal standard method as in Example 1, with the result that the conversion of MN was 90.2% and the selectivity to VK3 was 57.6%.

(2) Insolubilization and collection through filtration of palladium compound 39.2 ml of a 10% aqueous sodium hydroxide was added to the reaction solution obtained above to neutralize the sulfuric acid in the solution, followed by filtration of the precipitated salts primarily composed of sulfates.

The peroxide in the filtrate was quantitatively determined by the iodometry, revealing that the total active oxygen content in the filtrate was 24.8 mmols. 6.4 ml of an aqueous sodium sulfide having a concentration of 1 mol/liter was added to the filtrate and agitated at room temperature for 1 hour, followed by standing overnight and filtration of the resultant black precipitate (sulfur compound of palladium) with use of a filter paper. The filtrate was analyzed by an atomic absorption spectrometry. As a result, it was found that the content of palladium left in the filtrate was 1.5% of palladium used for the oxidation reaction.

(3) Solubilization of collected palladium compound

The black precipitate obtained above was washed with water, air-dried and placed in 20 ml of acetic acid together with the filter paper, followed by heating to 70° C. under agitation. 1.2 ml of a 60% aqueous hydrogen peroxide was added gradually in 1 hour, followed by further agitation at 70° C. for 1 hour. After cooling, the suspended pieces of the filter paper were removed by filtration and the filtrate was subjected to an atomic absorption spectrometry. As a result, it was found that palladium was contained in an amount of 11.40 mg present in 20.6 g of the filtrate. This corresponded to 96.2% of palladium (11.85 mg) used in the oxidation reaction.

(4) Isolation and purification of 2-methyl-1,4-naphthoquinone

The reaction solution from which the black precipitate had been removed by filtration was subjected to removal of the acetic acid under reduced pressure. 45 ml of butyl acetate and 45 ml of water were added to the remained solid matters. The butyl acetate phase was separated from the resulted solution and washed successively with 45 ml of water (once), 45 ml of a 5% aqueous sodium carbonate (thrice), a 1% aqueous acetic acid (once), and a 10% aqueous sodium sulfate (twice), followed by concentration by removal of the butyl acetate under reduced pressure. The concentrated solution was cooled and the precipitated crystals were obtained by filtration. The crystals were dried under reduced pressure to obtain 3.53 g of 2-methyl-1,4-naphthoquinone. This product was analyzed according to an HPLC internal standard method with a purity being 97.2%.

(5) Re-use of solubilized palladium compound

A mixture of 3.5 g (24.6 mmol) of 2-methylnaphthalene (MN), 80 ml of acetic acid and 4.0 g (40 g/liter of total acetic acid) of sulfuric acid was heated to 70° C., to which 16.3 ml (corresponding to 9.48 mg as palladium) of the filtrate obtained in (3) above under agitation. Immediately, a mixture of 3.5 ml (76.6 mmol) of a 60% aqueous hydrogen peroxide and 4.0 ml of acetic acid was added dropwise to the reaction solution in 15 minutes. After completion of the addition, the mixture was agitated at 70° C. for further 15 minutes. After cooling, the reaction solution was analyzed according to an HPLC internal standard method as in Example 1, revealing that the conversion of MN was 90.2% and the selectivity to VK3 was 58.8%.

Comparative Example 8

In the same manner as in (5) of Example 21, the oxidation reaction of 2-methylnaphthalene was conducted under similar reaction conditions except that a fresh palladium acetate was used as catalyst in place of the collected palladium compound from the reaction solution, with the same palladium concentration as in (5). The results of the reaction revealed that the conversion of MN was 89.9% and the selectivity to VK3 was 58.7%.

The comparison between Example 21 and Comparative Example 8 demonstrates that the collected palladium compound used in Example 21 has a similar catalytic activity as the fresh catalyst.

Example 22

A recycle test of a palladium compound (catalyst) was conducted according to the following procedure.

(1). Oxidation reaction of 2-methylnaphthalene (preliminary step)

300 ml of acetic acid was charged into a separable flask (first reactor) having an inner capacity of 1000 ml and equipped with an agitator, a thermometer, a charge port for starting materials and a discharge port, followed by continuous charge of the following three solutions A to C by means of a metering pump.

A: acetic acid solution of 2-methylnaphthalene (concentration: 140 g/l of 2-methylnaphthalene).

B: acetic acid solution of palladium acetate and sulfuric acid (concentrations: 0.4 g/l of palladium acetate, 80 g/l of sulfuric acid).

C: acetic acid solution of a 60% aqueous hydrogen peroxide (concentration: 200 g/l of hydrogen peroxide)

The charge rates of the respective solutions were such that solution A=5.08 g/minute, Solution B=5.36 g/minute, and solution C=5.4 g/minute.

At the time when the amount of the reaction solution in the first reactor reached 600 ml, the reaction solution began to be discharged by means of a metering pump so that the amount of the reaction solution in the first reactor may be kept constant and the discharged solution was continuously fed into a tubular reactor (second reactor) having an inner diameter of 0.5 cm and an inner capacity of 300 ml. The inner temperatures of the respective reactors were, respectively, maintained at 75° C.

In order that the composition of the reaction solution in the first reactor should be approached to the stationary state, the reaction was run continuously under the above conditions for 8 hours, after which the run was stopped while keeping the reaction solutions in the first and second reactors. The reaction solution discharged from the second reactors was separately treated and was not fed to the following steps.

(2) Oxidation reaction of 2-methylnaphthalene

The above mentioned reaction solutions in the first and second reactors were heated to 75° C. While the three fresh solutions A to C set out (1) above were, respectively, charged continuously into the first reactor at predetermined rates, the reaction solution in the first reactor was continuously fed to the second reactor so that the amount of the reaction solution in the first reactor was kept at a given constant level. The reaction was continued until the solution B (1000 ml) was fully consumed.

(3) Insolubilization and separation of the palladium compound

The reaction solution discharged from the second reactor was collected, after analyzed according to an HPLC internal standard method as in Example 1, to which a 50% aqueous sodium hydroxide was added until the pH of the reaction solution arrived at 2. After agitation for further 1 hour, the precipitated salt was removed by filtration. The filtrate was analyzed by the iodometry to determine an amount of the peroxide. An aqueous sodium sulfide was added to in an amount corresponding to ¼ equivalents of the amount of the peroxide determined by the analysis and agitated for 1 hour. The resulting black precipitate (sulfur compound of palladium) was filtered by use of a membrane filter. The precipitate was washed with water and dried.

(4) Solubilization of the collected palladium compound and preparation for re-use The black precipitate obtained in (3) above was suspended in 200 ml of acetic acid, to which a mixture of 100 ml of a 60% aqueous hydrogen peroxide and 100 ml of acetic acid was added dropwise so slowly that the temperature of the reaction mixture did not exceed 70° C. After completion of the addition, agitation was continued for 15 minutes. 80 g of sulfuric acid and 40 mg of palladium acetate (fresh catalyst) for making up for lost catalyst were added to the resultant solution of the palladium compound, to which acetic acid was further added to make a total amount of 1000 ml.

(5) Re-use of the solubilized palladium compound

The acetic acid solution containing the palladium compound obtained in (4) above was served as the solution B and the oxidation reaction of 2-methylnaphthalene as in (2) was conducted.

The reaction solution discharged from the second reactor was collected and subjected to treatments as in (3) and (4) above to collect the palladium compound. The thus obtained acetic acid solution containing the palladium compound was re-used as the solution B for the oxidation reaction of 2-methylnaphthalene as shown in (2).

The above procedure was repeated where the oxidation reaction of 2-methylnaphthalene of (2) was repeated ten times. The conversion of MN and the selectivity to VK3 in the respective runs are shown in Table 5.

TABLE 5

| Runs | Conversion of MN (%) | Selectivity to VK3 (%) | Yield of VK3 (%) |
|---|---|---|---|
| 1 | 90.2 | 57.5 | 51.9 |
| 2 | 91.0 | 57.7 | 52.5 |
| 3 | 90.5 | 57.0 | 51.6 |
| 4 | 90.3 | 58.2 | 52.6 |
| 5 | 92.0 | 57.5 | 52.9 |
| 6 | 91.5 | 58.1 | 53.2 |
| 7 | 90.8 | 59.7 | 54.2 |
| 8 | 91.0 | 59.3 | 54.0 |
| 9 | 90.4 | 58.0 | 52.4 |
| 10 | 91.0 | 58.0 | 52.8 |

As will be apparent from Table 5, the conversion of MN, selectivity to VK3 and yield of VK3 do not decrease owing to the repeated use of the palladium compound.

Obviously, numerous modifications and variations are possible in light of the above teachings. It is therefore to be understood that within the scope of the appended claims the present invention may be practiced otherwise than as specifically described herein.

What is claimed is:

1. A process for producing 2-methyl-1,4-naphthoquinone comprising reacting hydrogen peroxide and/or an organic peracid with 2-methylnaphthalene in a carboxylic acid solution in the presence of a palladium compound soluble in said carboxylic acid solution and 5 to 100 g of sulfuric acid per liter of the carboxylic acid solution, wherein said carboxylic acid solution is a liquid which is miscible with said hydrogen peroxide, organic peracid and sulfuric acid.

2. A process for producing 2-methyl-1,4-naphthoquinone according to claim 1, wherein said carboxylic acid is a saturated aliphatic carboxylic acid having not greater than 8 carbon atoms.

3. A process for producing 2-methyl-1,4-naphthoquinone according to claim 2, wherein said carboxylic acid is selected from the group consisting of acetic acid, propionic acid, butyric acid, caprylic acid, caproic acid and capric acid.

4. A process for producing 2-methyl-1,4-naphthoquinone according to claim 2, wherein said carboxylic acid is acetic acid.

5. A process for producing 2-methyl-1,4-naphthoquinone according to claim 1, wherein said palladium compound is selected from the group consisting of palladium acetate, palladium caprylate, palladium chloride, palladium bromide, palladium sulfate, palladium nitrate, palladium acetylacetonate, dichlorobis (triphenylphosphine) palladium, and tris (dibenzylideneacetone) dipalladium (0) chloroform adduct.

6. A process for producing 2-methyl-1,4-naphthoquinone according to claim 1, wherein said palladium compound is palladium acetate or palladium sulfate.

7. A process for producing 2-methyl-1,4-naphthoquinone according to claim 1, wherein said sulfuric acid is used in an amount of 15 to 50 g per liter of said carboxylic acid.

8. A process for producing 2-methyl-1,4-naphthoquinone according to claim 1, wherein said hydrogen peroxide is used in an amount of 1 to 4 mols per mole of said 2-methylnaphthalene.

9. A process for producing 2-methyl-1,4-naphthoquinone according to claim 1, comprising reacting hydrogen peroxide and/or an organic peracid with 2-methylnaphthalene in a solvent containing a carboxylic acid in the presence of a palladium compound and 5 to 100 g of sulfuric acid per liter of the carboxylic acid wherein the palladium compound in the reaction solution is collected and reused according to the following steps (a) to (d):

(a) adding a hydrogen sulfide gas, or a solution of hydrogen sulfide and/or a salt thereof to the reaction solution to convert the palladium compound used as a catalyst into an insoluble sulfur compound of palladium;

(b) separating the insoluble sulfur compound of palladium from the solution;

(c) oxidizing the thus separated sulfur compound of palladium with hydrogen peroxide and/or an organic peracid in a carboxylic acid solvent and dissolved therein; and (d) recycling the obtained carboxylic acid solution of the palladium compound for the oxidation reaction of 2-methylnaphthalene with hydrogen peroxide and/or an organic peracid.

* * * * *